United States Patent [19]

Buchecker et al.

[11] Patent Number: 5,800,734
[45] Date of Patent: *Sep. 1, 1998

[54] 1-FLUOROCYCLOHEXENE-DIFLUOROPHENYL DERIVATIVES

[75] Inventors: Richard Buchecker, Zurich, Switzerland; Guy Marck, Rixheim, France

[73] Assignee: Rolic AG, Zug, Switzerland

[*] Notice: The term of this patent shall not extend beyond the expiration date of Pat. No. 5,662,829.

[21] Appl. No.: 610,029

[22] Filed: Mar. 4, 1996

[30] Foreign Application Priority Data

Apr. 4, 1995 [CH] Switzerland ............ 00 948/95

[51] Int. Cl.[6] .................. C09K 19/34; C09K 19/12; C09K 19/30; C07C 19/08
[52] U.S. Cl. ............... 252/299.61; 252/299.01; 252/299.67; 252/299.63; 252/299.66; 252/299.64; 252/299.65; 560/65; 560/108; 549/369; 549/370; 568/647; 570/129
[58] Field of Search .................. 252/299.63, 299.01, 252/299.6, 299.66, 299.67, 299.61, 299.64, 299.65; 570/129; 568/647; 549/369, 370; 560/65, 108

[56] References Cited

U.S. PATENT DOCUMENTS

| | | | |
|---|---|---|---|
| 4,212,815 | 7/1980 | Boswell, Jr. .................. | 260/397.2 |
| 4,505,837 | 3/1985 | Romer et al. .................. | 252/299.6 |
| 4,910,350 | 3/1990 | Tanaka et al. .................. | 570/129 |
| 4,946,986 | 8/1990 | Tanaka et al. .................. | 558/411 |
| 5,209,868 | 5/1993 | Reiffenrath et al. .................. | 252/299.63 |
| 5,254,698 | 10/1993 | Coates et al. .................. | 549/369 |
| 5,356,560 | 10/1994 | Reiffenrath et al. .................. | 252/299.61 |
| 5,399,292 | 3/1995 | Buchecker et al. .................. | 252/299.63 |
| 5,447,658 | 9/1995 | Buchecker et al. .................. | 252/299.6 |
| 5,560,863 | 10/1996 | Reiffenrath et al. .................. | 252/299.01 |

FOREIGN PATENT DOCUMENTS 44 15 881 A1  5/1994  Germany.

OTHER PUBLICATIONS

Chem. Abstract vol. 111, No. 6, abstr. No. 048298 (1989).
Chem. Abstract vol. 100, No. 14, abstr. No. 125657 (1989).
Organic Reactions vol. 35, p. 531 (1988).

*Primary Examiner*—C. H. Kelly
*Attorney, Agent, or Firm*—Bryan Cave LLP

[57] ABSTRACT

A compound of the formula

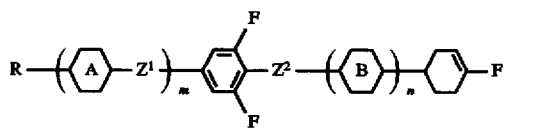

wherein

R is $C_1$–$C_7$ alkyl or $C_2$–$C_{12}$ alkenyl; rings A and B each independently are 1,4-phenylene, trans-1,4-cyclohexylene or trans-1,3-dioxane-2,5-diyl;

$Z^1$ is a single bond or —$CH_2CH_2$—; and $Z^2$ is a single bond, —$CH_2CH_2$—, —$OCH_2$—, —C≡C—, —COO— or —OOC—; and m, n are 0 or 1, with the proviso that m+n≦1;

as well as liquid crystalline mixtures which contain such compounds and the use of such compounds and, respectively, mixtures for electro-optical display devices.

16 Claims, No Drawings

1-FLUOROCYCLOHEXENE-DIFLUOROPHENYL DERIVATIVES

FIELD OF THE INVENTION

The present invention is concerned with novel liquid crystalline 1-fluorocyclohexene-difluorophenyl derivatives as well as liquid crystalline mixtures which contain such compounds and the use of such compounds and mixtures in electro-optical devices.

BACKGROUND

Liquid crystals are used primarily as dielectrics in display devices, since the optical properties of such substances can be influenced by an applied voltage. Electro-optical devices based on liquid crystals will be well-known to a person skilled in the art and can be based on various effects. Such devices are, for example, cells having dynamic scattering, DAP cells (deformation of aligned phases), guest/host cells, TN cells having a "twisted nematic" structure, STN cells ("super twisted nematic"), SBE cells ("super birefringence effect") and OMI cells ("optical mode interference"). For displays having a high content of information, actively controlled cells, e.g. TFT cells ("thin film transistor"), have in particular recently become important in addition to passively controlled, multiplexed cells. The most common display devices are based on the Schadt-Helfrich effect and have a twisted nematic structure.

The liquid crystal materials must have a good chemical, photochemical and thermal stability and a good stability towards electric fields. Further, they should have a suitable mesophase over a range which is as broad as possible (for example, a nematic or a cholesteric phase for the cells referred to above), but in spite of a sufficiently low viscosity should permit short response times, low threshold potentials and a high contrast in the cells. Further properties such as the electrical conductivity, the dielectric anisotropy and the optical anisotropy must fulfil different requirements depending on the field of application and type of cell. For example, materials for cells having a twisted nematic structure should have a positive dielectric anisotropy which is as high as possible and at the same time should have a conductivity which is as low as possible. This latter property is of particular importance for TFT cells. Unfortunately, however, components having a high dielectric anisotropy mainly lead to an increased conductivity in mixtures because of their better capacity to dissolve ionic impurities. Accordingly, components which are distinguished by a dielectric anisotropy which is as high as possible with simultaneously a conductivity which is as low as possible are sought after.

SUMMARY OF THE INVENTION

Compounds of the formula

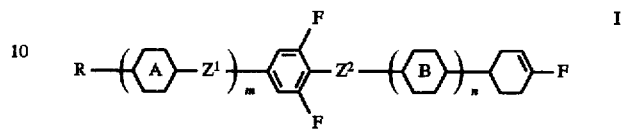

wherein

R is $C_1$–$C_{12}$ alkyl or $C_2$–$C_{12}$ alkenyl;

rings A and B each independently are 1,4-phenylene, trans-1,4-cyclohexylene or trans-1,3-dioxane-2,5-diyl;

$Z^1$ is a single bond or —$CH_2CH_2$—; and $Z^2$ is a single bond, —$CH_2CH_2$—, —$OCH_2$—, —C≡C—, —COO— or —OOC—; and m, n are 0 or 1, with the proviso that m+n≤1.

The compounds of formula I all have, in spite of low polarity, a low threshold potential ($V_{10}$) and are therefore especially suitable for use in TFT cells.

DETAILED DESCRIPTION OF THE INVENTION

The term "$C_1$–$C_{12}$ alkyl or $C_2$–$C_{12}$ alkenyl" are straight-chain or branched (optionally chiral) alkyl residues, straight-chain 3E-alkenyl or alkenyl residues having a terminal double bond or on a saturated ring such as trans-1,4-cyclohexylene or trans-1,3-dioxane-2,5-diyl also 1E-alkenyl residues. These residues have a maximum of 12, preferably a maximum of 7, carbon atoms. These are, for example, alkyl residues such as methyl, ethyl, propyl, butyl, pentyl, hexyl, heptyl, isopropyl, 2-methyl-butyl, 2-methyl-pentyl or 2-methyl-hexyl; 1E-alkenyl residues such as 1E-propenyl, 1E-butenyl, 1E-pentenyl, 1E-hexenyl or 1E-heptenyl; 3E-alkenyl residues such as 3E-pentenyl, 3E-hexenyl or 3E-heptenyl; or alkenyl residues such as residues having a terminal double bond such as vinyl, 3-butenyl, 4-pentenyl, 5-hexenyl or 6-heptenyl.

Preferred are compounds of the formulas

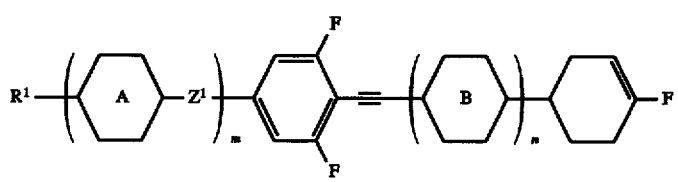

I-A

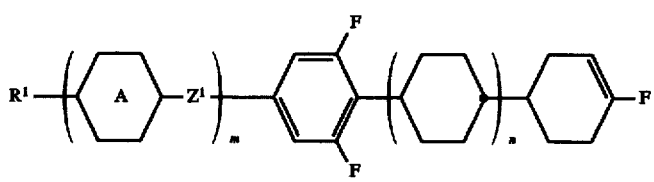

I-B

-continued

I-C
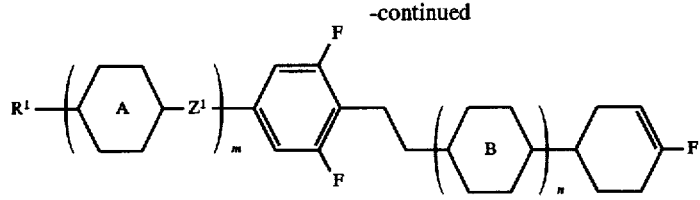

I-D
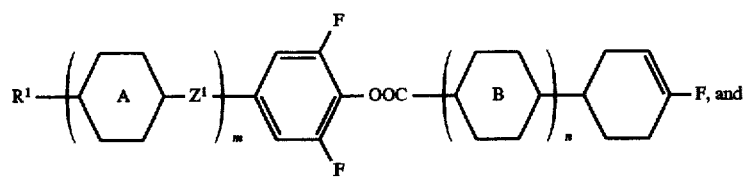
F, and

I-E
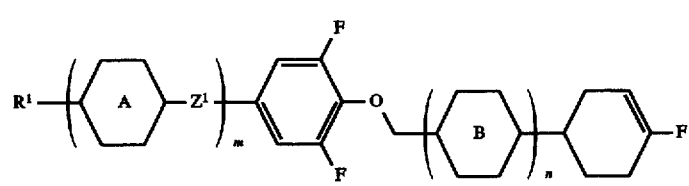

wherein A, $Z^1$, B, m and n are as defined above; and $R^1$ is $C_1$–$C_7$ alkyl, $C_4$–$C_7$ 3E-alkenyl or on a saturated ring also vinyl or $C_2$–$C_7$ 1E-alkenyl.

Preferred compounds of formula I-A are those in which $Z^1$ is a single bond as well as compounds in which ring B is trans-1,4-cyclohexylene, that is, compounds of the formulas I-A1
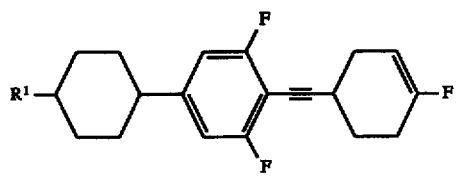

I-A2
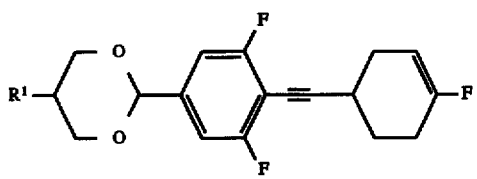

I-A3
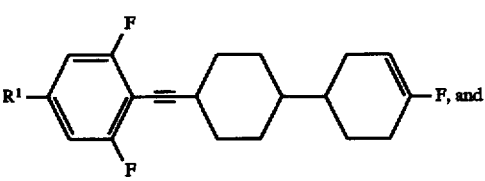
F, and

I-A4
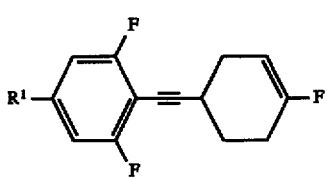

wherein $R^1$ is $C_1$–$C_7$ alkyl, $C_4$–$C_7$ 3E-alkenyl or on a saturated ring also vinyl or $C_2$–$C_7$ 1E-alkenyl.

Preferred compounds of formula I-B are

I-B1
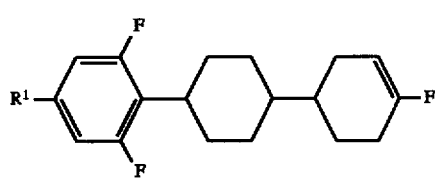

I-B2
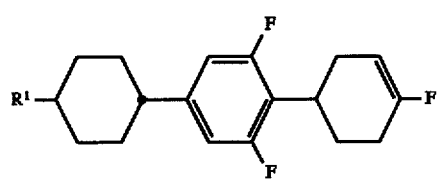

I-B3
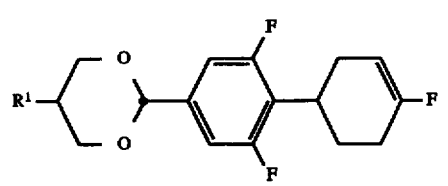

I-B4
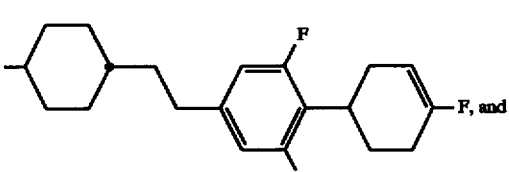
F, and

I-B5
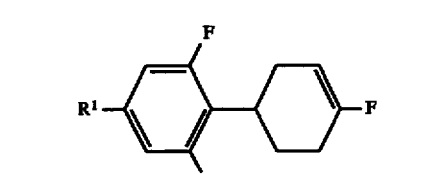

wherein $R^1$ is $C_1$–$C_7$ alkyl, $C_4$–$C_7$ 3E-alkenyl or on a saturated ring also vinyl or $C_2$–$C_7$ E-alkenyl.

Especially preferred compounds of formula I-C are those in which $Z^1$ is a single bond, that is, compounds of the formula

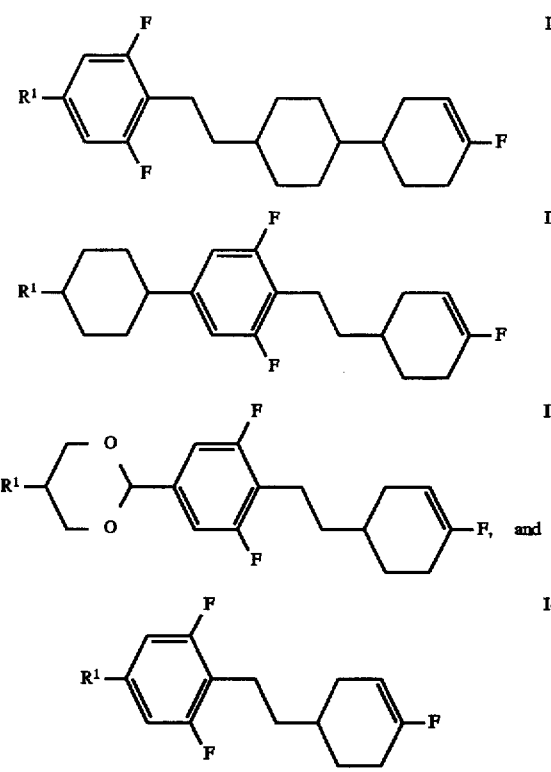

I-C1

I-C2

I-C3

I-C4 wherein $R^1$ is $C_1$–$C_7$ alkyl, $C_4$–$C_7$ 3E-alkenyl or on a saturated ring also vinyl or $C_2$–$C_7$ E-alkenyl.

Preferred compounds of formula I-D are compounds of the formulas

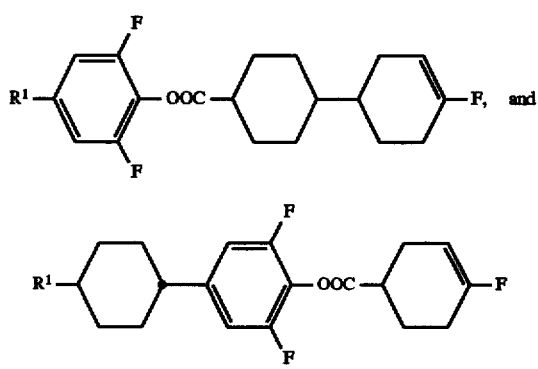

I-D1

I-D2 wherein $R^1$ is $C_1$–$C_7$ alkyl, $C_4$–$C_7$ 3E-alkenyl or on a saturated ring also vinyl or $C_2$–$C_7$ 1E-alkenyl.

Preferred compounds of formula I-E are compounds of the formulas

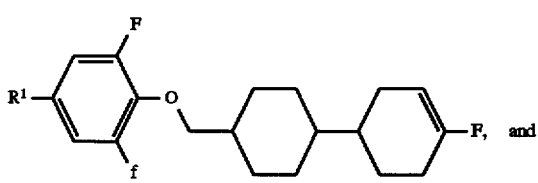

I-E1

I-E2 wherein $R^1$ is $C_1$–$C_7$ alkyl, $C_4$–$C_7$ 3E-alkenyl or on a saturated ring also vinyl or $C_2$–$C_7$ 1E-alkenyl.

The compounds of formula I can be produced in a known manner. Thus, for example, compounds of formula I-A can be produced from a correspondingly substituted cyclohexanone (1), which are known or can be prepared according to known methods. The cyclohexanone (1) is converted into the corresponding 1-fluorocyclohexene (2) with diethylaminosulphur trifluoride (DAST) analogously to a procedure described in U.S. Pat. No. 4,212,815 or in Organic Reactions 35, 531 (1988), both incorporated by reference herein. The reaction is preferably carried out in polar aprotic and inert solvents such as dimethoxyethane, diglyme, dioxan and the like at temperatures from about 20° C. to about 50°C. The formation of geminal difluorocyclohexane derivatives can be suppressed by adding a catalytic amount of acid such as oleum or trifluoromethane-sulphonic acid. The further reaction steps, starting from 2, which lead to the acetylenes of formula IA are known, for example, in EP 593 997 incorporated by reference herein and are outlined in Scheme 1.

The compounds of formula I-B in which n is 0 can be prepared starting from a correspondingly substituted difluoro-phenyl (7), which are known or can be prepared according to known methods. The difluorophenyl (7) is reacted with 1,4-dioxaspiro[4.5]decan-8-one (8) which is known, in the presence of butyllithium. The compounds of formula I-B in which n is 1 can be prepared by reacting the correspondingly substituted difluorophenyl (7l) with 4-(1, 4-dioxaspiro[4.5]dec-8-yl)-cyclohexanone (9) which is known, as outlined in Scheme 2.

Compounds of formula I-C can be prepared, for example, analogously to the compounds of formula I-A, but in this case the keto group of 1 is conveniently protected according to known methods. The keto group is then liberated and subsequently fluorinated only after the reduction of the triple bond (15→16), see Scheme 3.

The production of compounds of formula I-D and I-E can be effected in a known manner as outlined, for example, in Scheme 4.

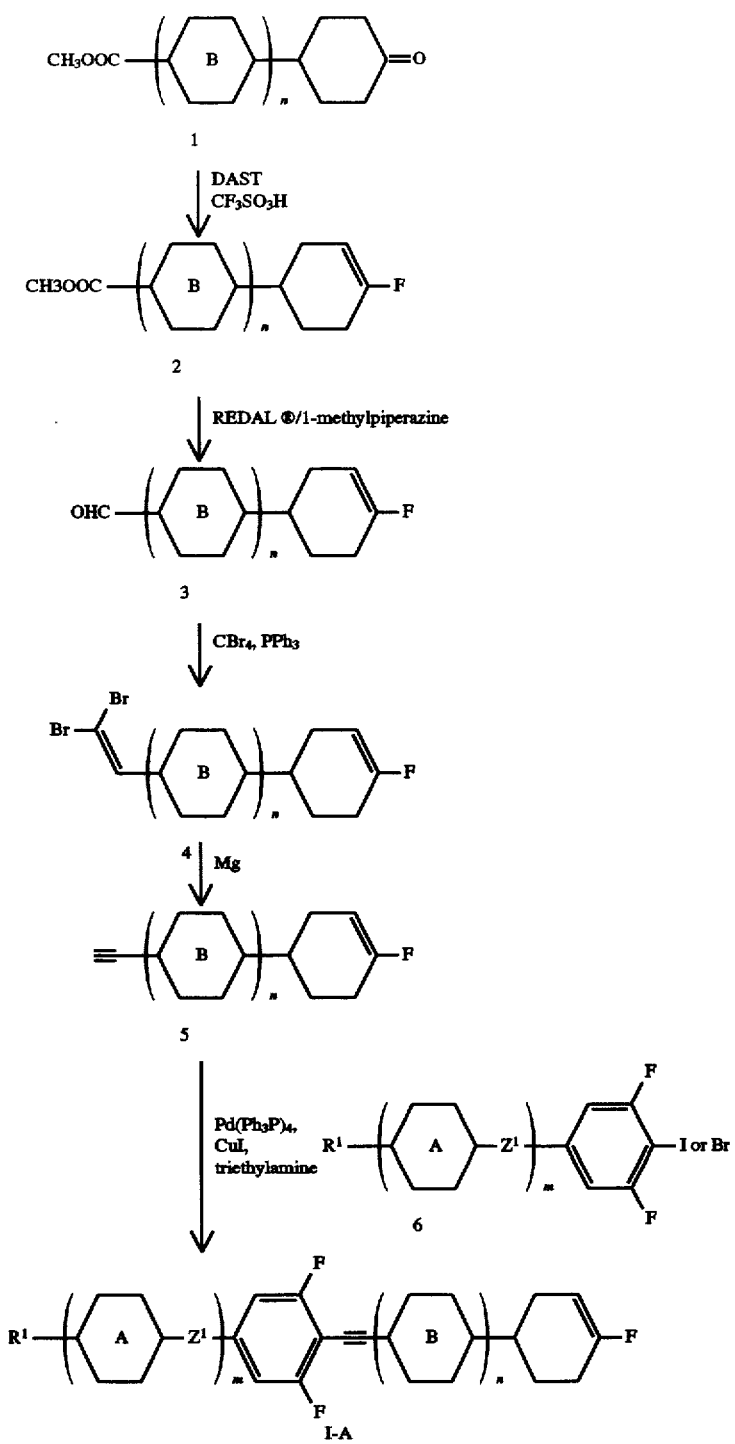
Scheme 1

Scheme 2
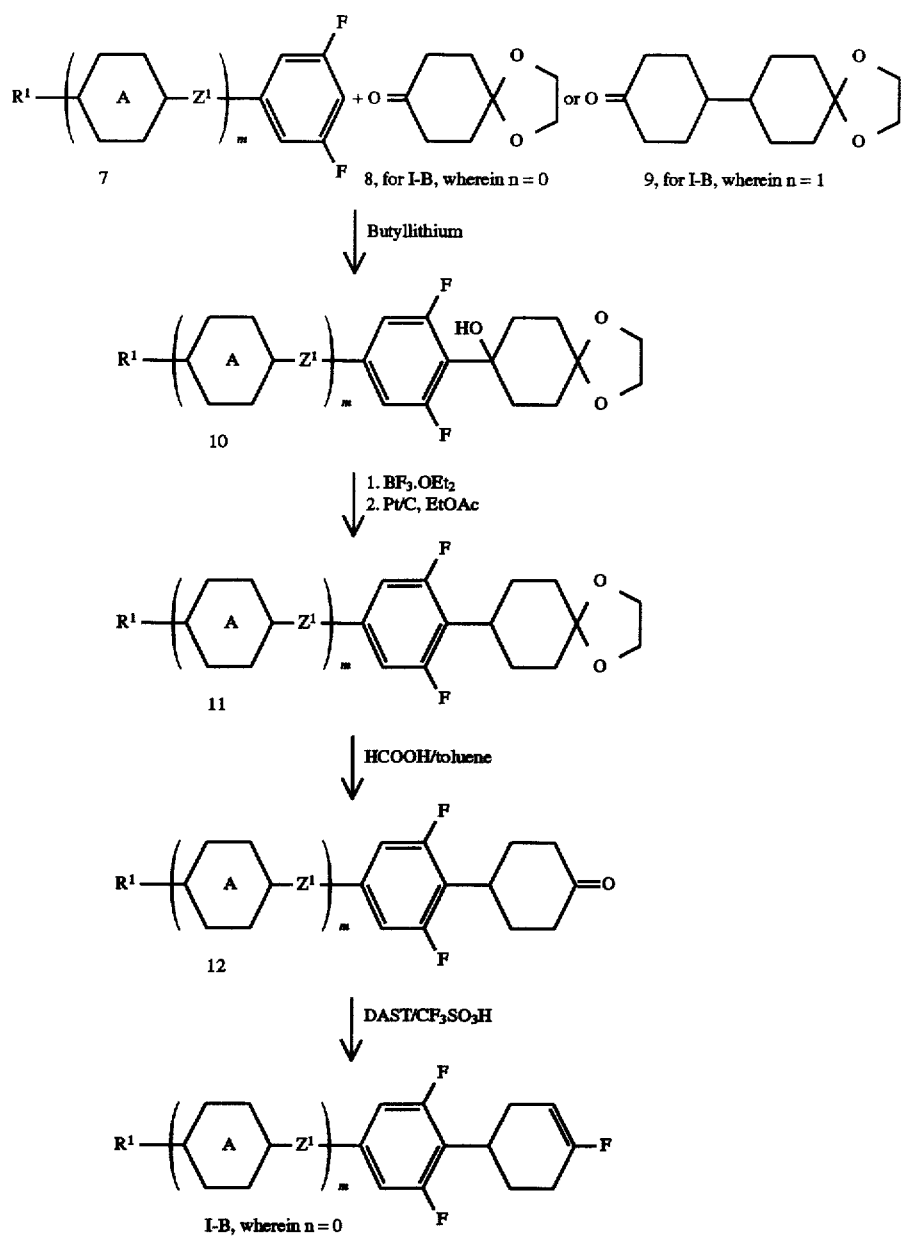
Scheme 3
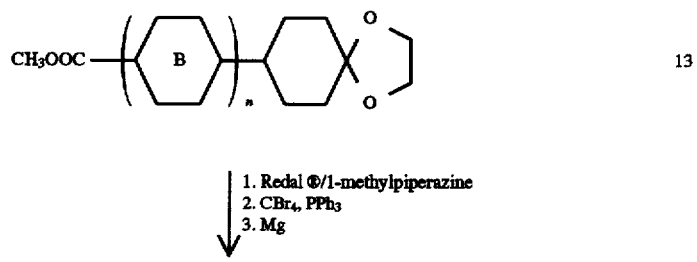

-continued
Scheme 3
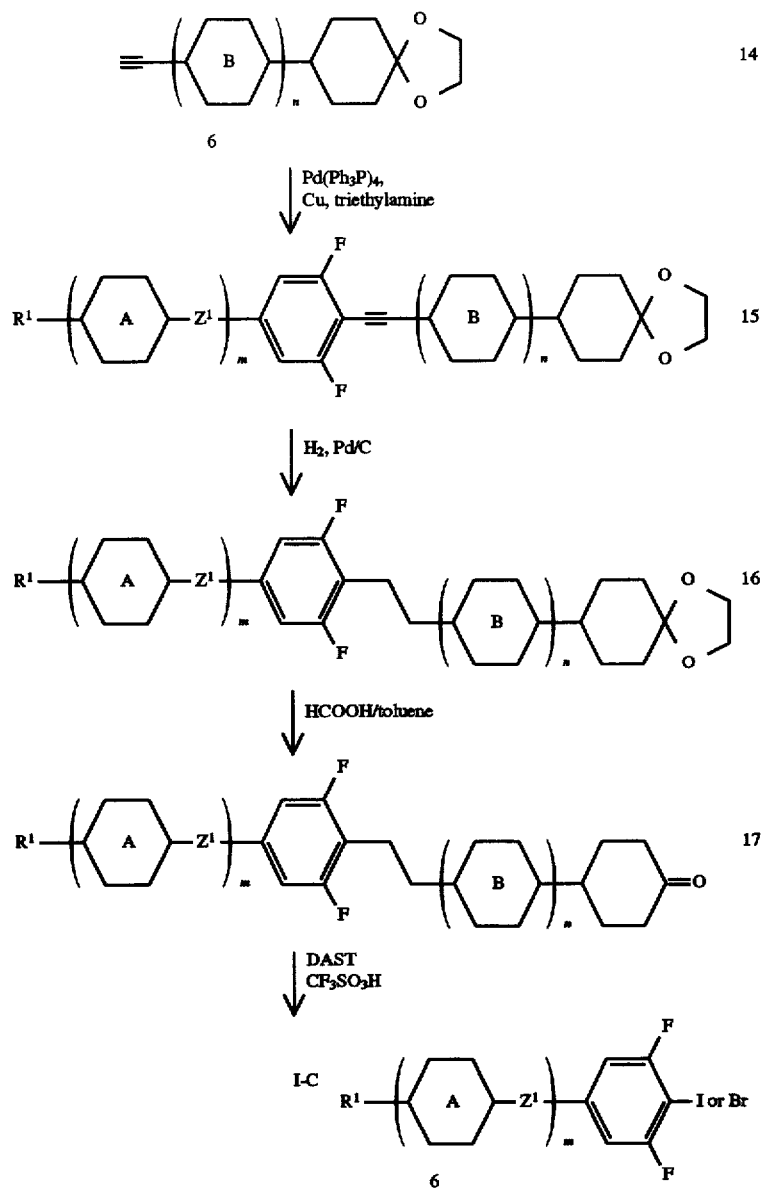
Scheme 4
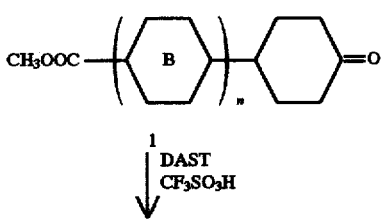

-continued
Scheme 4

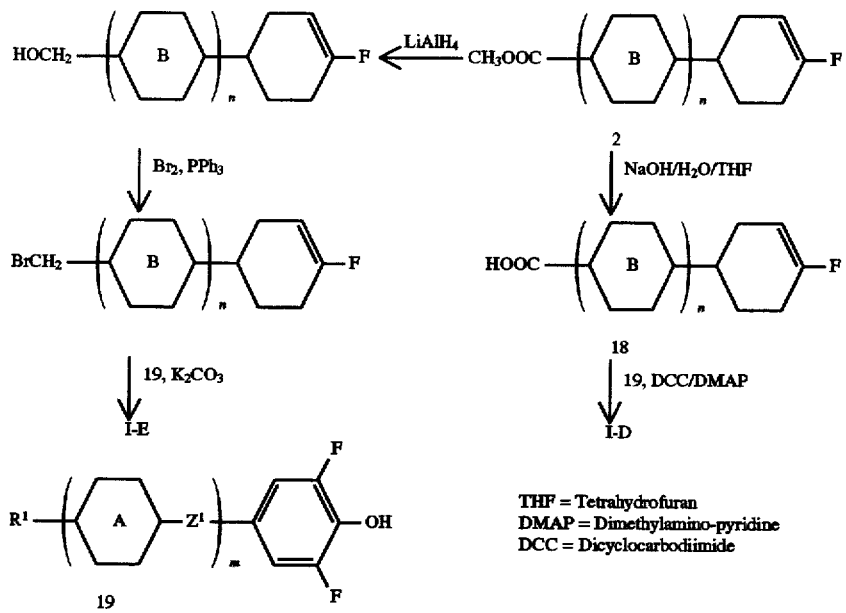

THF = Tetrahydrofuran
DMAP = Dimethylamino-pyridine
DCC = Dicyclocarbodiimide

The compounds of formula I can be used in the form of mixtures with one another and/or with other liquid crystal components. The invention is therefore also concerned with liquid crystalline mixtures having at least 2 components, of which at least one component is a compound of formula I. A second component and optionally further components can be additional compounds of general formula I or other suitable liquid crystal components. Suitable liquid crystal components are known, for example, from D. Demus et al., Flüssige Kristalle in Tabellen, VEB Deutscher Verlag für Grundstoffindustrie, Leipzig, volumes I and II and, many of them are commercially available.

Having regard to the good solubility of the compounds of formula I in accordance with the invention in other liquid crystal materials and having regard to their good miscibility with one another, the content of compounds of formula I in the mixtures in accordance with the invention can be relatively high and can be, for example, 1–70 wt.%. In general, a content of about 3–40 wt.%, especially of about 5–20 wt.%, of compounds of formula I is preferred.

The mixtures in accordance with the invention preferably contain, in addition to one or more compounds of formula I, one or more compounds from the group of compounds of the formulas

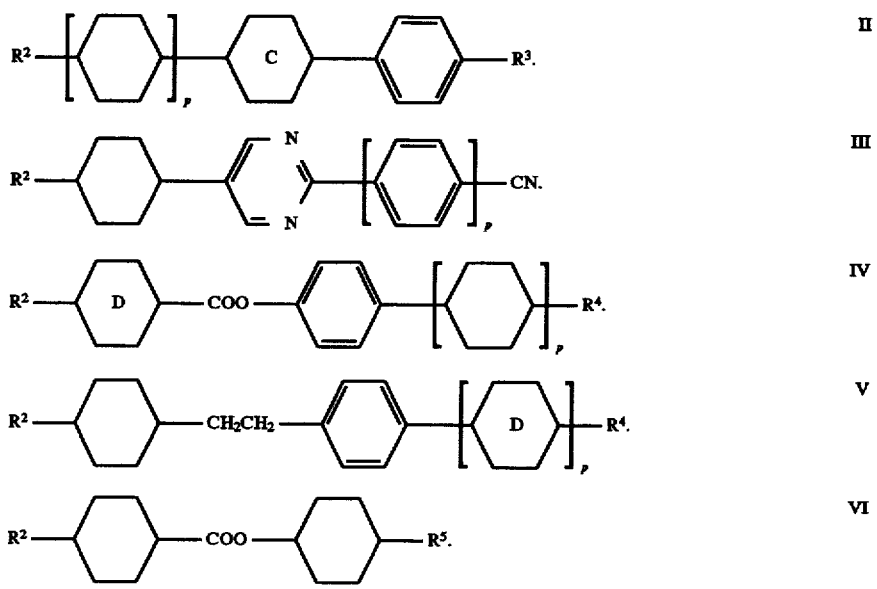

-continued

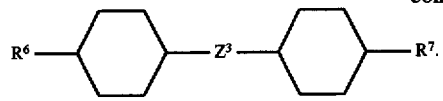   VII

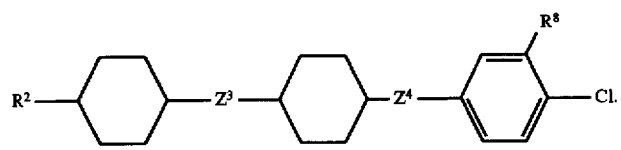   VIII

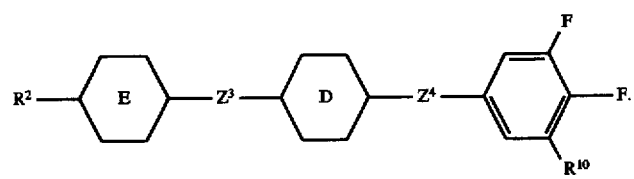   IX

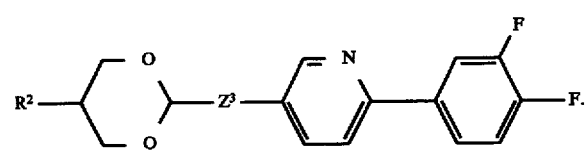   X

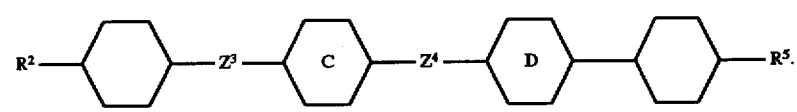   XI

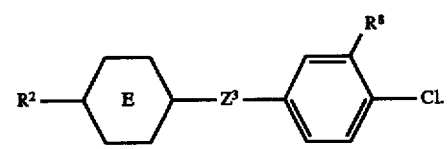   XII

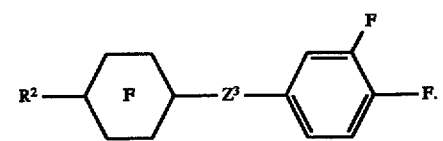   XIII

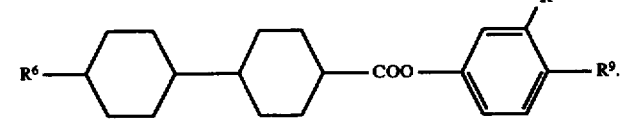   XIV

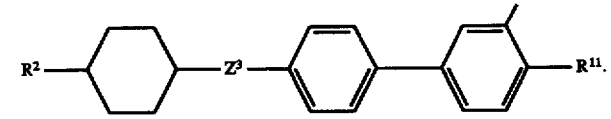   XV

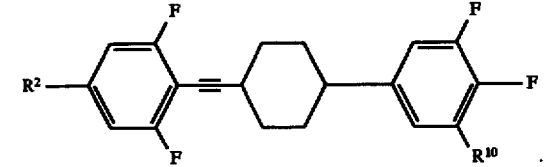   XVI wherein $R^2, R^5$ are alkyl, alkoxyalkyl, 3E-alkenyl, 4-alkenyl or on a saturated ring also 1E-alkenyl;

p is 0 or 1;

ring C is 1,4-phenylene, pyridine-2,5-diyl, pyrimidine-2,5-diyl, trans- 1,4-cyclohexylene or trans-1,3-dioxane-2,5-diyl;

$R^3$ is cyano, isothiocyanato, fluorine, alkyl, 3E-alkenyl, 4-alkenyl, alkoxy, 2E-alkenyloxy, 3-alkenyloxy or 1-alkynyl;

ring D is 1,4-phenylene or trans-1,4-cyclo-hexylene;

$R^4$ is alkyl, 3E-alkenyl, 4-alkenyl or on trans-1,4-cyclohexylene also 1E-alkenyl or on 1,4-phenylene also cyano, isothiocyanato, alkoxy, 2E-alkenyloxy or 3-alkenyloxy;

$R^6$ is alkyl, 1E-alkenyl, 3E-alkenyl or 4- alkenyl;

$R^7$ is cyano, alkyl, 1E-alkenyl, 3E-alkenyl, 4-alkenyl, alkoxy, 2E-alkenyloxy, 3-alkenyloxy, alkoxymethyl or (2E-alkenyl)oxymethyl;

$Z^3, Z^4$ are a single bond or —$CH_2CH_2$—, with two aromatic rings always being linked by a single bond;

ring E is trans-1,4-cyclohexylene or trans-1,3-dioxane-2,5-diyl;

$R^8$ is hydrogen, fluorine or chlorine;

$R^9$ is cyano, fluorine or chlorine;

$R^{10}$ is hydrogen or fluorine;

$R^{11}$ is fluorine or chlorine; and ring F is pyrimidine-2,5-diyl, trans-1,4-cyclo-hexylene or trans-1,3-dioxane-2,5-diyl.

The terms alkyl, 1E-alkenyl, 3E-alkenyl and alkenyl having a terminal double bond used in connection with the compounds of formulas II to XVI are defined as described above for the compounds of formula I; "4-alkenyl" is preferably straight-chain alkenyl residues with a maximum of 12 carbon atoms, in which the double bond is situated in the 4-position, such as, for example, 4-pentenyl, 4-hexenyl or 4-heptenyl.

"Aromatic rings" is rings such as, for example, 1,4-phenylene, pyridine-2,5-diyl or pyrimidine-2,5-diyl.

"Saturated rings" is trans-1,4-cyclohexylene or trans-1,3-dioxane-2,5-diyl.

"Alkyloxyalkyl" is preferably straight-chain residues with a maximum of 12 carbon atoms such as, for example, methoxy-methyl, ethoxymethyl, propyloxymethyl, butyloxymethyl and the like.

"Alkyloxy" is preferably straight-chain residues with a maximum of 12 carbon atoms such as, for example, methoxy, ethoxy, propyloxy, butyloxy, pentyloxy, hexyloxy, heptyloxy and the like.

"2E- or 3-Alkenyloxy" is preferably straight-chain alkenyl-oxy residues with a maximum of 12 carbon atoms in which the double bond is situated in the 2- or, respectively, 3-position and E or Z indicates the preferred configuration, such as, for example, allyloxy, 2E-butenyloxy, 2E-pentenyloxy, 2E-hexenyloxy, 2E-heptenyloxy, 3-butenyloxy, 3-pentenyloxy, 3-hexenyloxy, 3-heptenyloxy, 4-pentenyloxy, 5-hexenyloxy, 6-heptenyloxy and the like.

"1-Alkynyl" is preferably straight-chain alkynyl residues with a maximum of 12 carbon atoms, in which the triple bond is situated in the 1-position, such as, for example, ethynyl, 1-propynyl, 1-butynyl, 1-pentynyl and the like.

The mixtures in accordance with the invention can also contain optically active compounds (e.g. optically active 4'-alkyl or 4'-alkoxy-4-biphenylcarbonitriles) and/or dichroic colouring substances (e.g. azo, azoxy or anthraquinone colouring substances). The content of such compounds is determined by the solubility, the desired helical pitch, colour, extinction and the like. In general, the content of optically active compounds and dichroic colouring substances is a maximum of in each case about 10 wt. % in the final mixture.

The production of the liquid crystalline mixtures and of the electro-optical devices can be effected in a known.

The production of the compounds of formula I as well as liquid crystalline mixtures containing these compounds is illustrated in more detail by the following Examples. C is a crystalline phase, S is a smectic phase, N is a nematic phase and I is the isotropic phase. $V_{10}$ denotes the voltage for 10% transmission (viewing direction perpendicular to the plate surface). $t_{on}$ and $t_{off}$ denote the switching-on time and, respectively, the switching-off time and Dn denotes the optical anisotropy.

EXAMPLE 1 a) Firstly 50 ml of dimethoxyethane and subsequently 200 ml of trifluoromethanesulphonic acid were added at room temperature to 5.0 g of 4-(trans-4-methoxycarbonylcyclohexyl)cyclo-hexanone in a flask which had been dried and gassed with nitrogen. After 5 minutes at room temperature 2.82 ml of dimethylaminosulphur trifluoride were added. After stirring at room temperature for 20 hours the reaction solution was partitioned between saturated $NaHCO_3$ solution and methylene chloride. The organic phase was separated and washed with a sodium carbonate solution and then with water. The aqueous phases were each individually extracted twice with methylene chloride. The organic phases were combined, dried over magnesium sulfate, filtered and the filtrate was evaporated. The crude product (7.25 g) was purified by chromatography on 250 g of silica gel. Eluent: toluene. This gave 1.46 g of 1-fluoro-4-(trans-4-methoxycarbonylcyclohexyl)cyclohex-1 -ene.

b) 0.84 g of 1-fluoro-4-(trans-4-methoxycarbonylcyclohexyl)cyclohex-1-ene was added to a solution of 0.7 g of sodium hydroxide in 10 ml of water and 20 ml of tetrahydrofuran in a sulphonation flask while gassing with nitrogen and the mixture was stirred at 60° C. for 20 hours. The reaction solution was poured into 2N hydrochloric acid and extracted with methylene chloride. The organic phase was washed twice with water. The aqueous phases were individually extracted twice with methylene chloride. The organic phases were combined, dried over magnesium sulfate, filtered and the filtrate was evaporated. This gave 0.79 g of white 1-fluoro-4-(trans-4-carboxycyclo-hexyl)cyclohex-1-ene, which was used in the next step without further purification.

c) The crude product from b), 0.79 g of 1-fluoro-4-(trans-4-carboxycyclohexyl)cyclohex-1-ene, was cooled to 0°C. under nitrogen together with 0.66 g of 2,6-difluoro-4-propylphenol and 60 mg of dimethylaminopyridine in 10 ml of methylene chloride and treated within 45 minutes with a solution of 1.0 g of dicyclohexyl-carbodiimide in 5 ml of methylene chloride. After stirring at room temperature for 30 minutes the white suspension was filtered over a Celite/silica gel pad. The filtrate was evaporated completely and gave 1.5 g of trans-4-(1-fluoro-cyclohex- 1 -en-4-yl) cyclohexanecarboxylic acid 2,6-difluoro-4-propylphenyl ester, which gave 0.62 g of white crystals by repeated recrystallization from hexane. M.p. (C/N) 58.40°C., c.l.p. (N/I) 96.1°C.

The following compounds can be prepared in an analogous manner:

trans-4-( 1 -fluorocyclohex- 1 -en-4-yl) cyclohexanecarboxylic acid 2,6-difluoro-4-pentylphenyl ester;

trans-4-(1-fluorocyclohex-1-en-4-yl) cyclohexanecarboxylic acid 2,6-difluoro-4-(3-butenyl) phenyl ester;

4-fluorocyclohex-3-enecarboxylic acid 2,6-difluoro-4-(trans-4-propylcyclohexyl)phenyl ester;

4-fluorocyclohex-3-enecarboxylic acid 2,6-difluoro-4-(trans-4-pentylcyclohexyl)phenyl ester.

EXAMPLE 2 a) 3.9 g of tetrabromomethane were dissolved in 30 ml of methylene chloride while gassing with nitrogen, cooled to 0°0 C. and treated within 15 minutes with a solution of 6.2 g of triphenyl-phosphine in 15 ml of methylene chloride. The solution was stirred at 0° C. and subsequently treated at 0°C. within 15 minutes with a solution of 1.25 g of trans-4-(1-fluorocyclohexen-4-yl) cyclohexane-carboxaldehyde in 8 ml of methylene chloride. After 1 hour at 0° C. the orange reaction solution was poured into 100 ml of pentane and the suspension was filtered. After evaporation the filtrate gave 3.0 g of crude product as a colourless liquid. This was taken up in cyclohexane and treated at 50° C. within 15 minutes with 5 ml of 30% hydrogen peroxide. The suspension was extracted three times with methanol/water 3:2. The aqueous phases were individually extracted twice with cyclohexane. The organic phases were combined, dried over magnesium sulfate, filtered and the filtrate was evaporated. This gave 1.89 g of colourless trans-1-(2,2-dibromovinyl)-4-(1-fluorocyclohex- 1 -en-4-yl)cyclohexane.

b) 0.138 g of Mg shavings was dried while gassing with nitrogen, covered with 2 ml of dry tetrahydrofuran, heated to 60° C. and activated with 2 iodine crystals. A solution of 1.89 g of trans- 1-(2,2-dibromovinyl)-4-( 1 -fluorocyclohex- 1 -en-4-yl)cyclohexane in 20 ml of tetrahydrofuran was added dropwise within 30 minutes. After 2 hours at 60° C. the reaction mixture was cooled to room temperature and partitioned between water and ether. The organic phase was washed twice with water. The aqueous phases were individually extracted twice with ether. The organic phases were combined, dried over magnesium sulfate, filtered and the filtrate was evaporated completely. The crude product was purified on silica gel with cyclohexane and gave 0.83 g of trans-1-ethynyl-4-(1-fluorocyclohex-1-en-4-yl)-cyclohexane.

c) 0.8 g of trans-1-ethynyl-4-(1-fluorocyclohex-1-en-4-yl)-cyclohexane and 1.0 g of 1-iodo-2,6-difluoro-4-propylbenzene were placed in 10 ml of triethylamine while gassing with nitrogen and treated with 0.128 g of tetrakis(triphenyl-phosphine)palladium(O) and 14 mg of copper(I) iodide. The reaction mixture was held at reflux for 17 hours. After cooling the reaction mixture was partitioned between water and ether. The organic phase was washed twice with water. The aqueous phases were individually extracted twice with ether. The ether phases were combined, dried over magnesium sulfate, filtered and the filtrate was evaporated. The brown crude product was purified on 100 g of silica gel with cyclohexane. The product-containing fractions were evaporated and the residue was recrystallized from isopropanol. This gave 0.57 g of white 1-fluoro-4-[trans-4-(2,6-difluoro-4-propylphenylethynyl) cyclohexyl]cyclohex-1-ene, m.p. (C/N) 74.2° C., cl.p. (N/I) 100.7° C.

The following compounds can be prepared in an analogous manner:

1-fluoro-4-[trans-4-(2,6-difluoro-4-ethylphenylethynyl) cyclo-hexyl] cyclohex-1-ene;

1 -fluoro-4- [trans-4-(2,6-difluoro-4-butylphenylethynyl) cyclo-hexyl] cyclohex- 1 -ene 1 -fluoro-4-[trans-4-(2,6-difluoro-4-pentylphenylethynyl) cyclo-hexyl] cyclohex- 1 -ene;

1-fluoro-4-[2,6-difluoro-4-(4-trans-ethylcyclohexyl) phenyl-ethynyl] cyclohex- 1 -ene;

1 -fluoro-4-[2,6-difluoro-4-(4-trans-propylcyclohexyl) phenyl-ethynyl] cyclohex-1-ene;

1-fluoro-4-[2,6-difluoro-4-(4-trans-(E)-propenylcyclohexyl)-phenylethynyl] cyclohex-1-ene;

1 -fluoro-4-[2,6-difluoro-4-(5-trans-propyl- 1 ,3-dioxan-2-yl)phenylethynyl] cyclohex-1 -ene;

1-fluoro-4-[2,6-difluoro-4-(5-trans-pentyl- 1 ,3-dioxan-2-yl)phenylethynyl] cyclohex-1 -ene;

1 -fluoro-4-[2,6-difluoro-4-(5-trans-(E)-propenyl- 1,3 -dioxan-2-yl)phenylethynyl] cyclohex-1-ene;

1 -fluoro-4- {2,6-difluoro-4- [5-trans-(3-butenyl)- 1 ,3-dioxan-2-yl] phenylethynyl} cyclohex-1 -ene.

EXAMPLE 3 a) A solution of 0.5 g of 2,6-difluoro-4-propylbenzene in 5 ml of tetrahydrofuran was cooled to −70° and treated within 20 minutes with 2.2 ml of 1.6M butyllithium. After 1 hour at −70° a solution of 0.5 g of 1,4-dioxaspiro[4,5]decan-8-one in 5 ml of tetrahydrofuran was added dropwise within 15 minutes. The reaction mixture was warmed slowly to room temperature and stirred for a further hour. The solution was subsequently treated with 10 ml of 10 percent acetic acid and partitioned between water and ethyl acetate. The organic phase was washed once with sodium carbonate solution and once with water. The aqueous phases were extracted individually twice with ethyl acetate. The organic phases were combined, dried over magnesium sulfate, filtered and the filtrate was evaporated completely. This gave 1.0 g of crude 8-(2,6-difluoro-4-propyl-phenyl)-8-hydroxy-1,4-dioxa-spiro[4,5]decane.

b) A solution of 1.0 g of 8-(2,6-difluoro-4-propylphenyl)-8-hydroxy-1,4-dioxa-spiro[4,5]decane in 25 ml of methylene chloride was cooled to 0° and treated with 440 ml of boron trifluoride etherate. After stirring at 0° for 1 ½ hours the reaction solution was treated with 25 ml of sodium carbonate solution and subsequently partitioned between water and methylene chloride. The organic phase was washed twice with sodium chloride solution. The aqueous phases were individually extracted twice with methylene chloride. The methylene chloride phases were combined, dried over magnesium sulfate, filtered and the filtrate was evaporated completely. This gave 1.0 g of 8-(2,6-difluoro-4-propylphenyl)-1,4-dioxa-spiro[4,5]dec-7-ene as a yellow oil.

c) The product of the foregoing step, 0.970 g of 8-(2,6-difluoro-4-propylphenyl)- 1 ,4-dioxa-spiro[4,5]dec-7-ene, was dissolved in 10 ml of ethyl acetate and hydrogenated in the presence of 0.200 g of 5% Pt/C. The hydrogenation was terminated after 5 hours. Thereafter, the suspension was filtered and the filtrate was evaporated completely. This gave 0.740 g of 8-(2, 6-difluoro-4-propylphenyl)-I,4-dioxa-spiro[4,5]decane as a white solid substance.

d) The hydrogenated product of the foregoing step, 0.74 g of 8-(2,6-difluoro-4-propylphenyl)-1,4-dioxa-spiro [4,5]decane, was taken up in 4 ml of 98% formic acid and 8 ml of toluene and stirred for 1 hour, thereafter the reaction solution was partitioned between water and ether. The organic phase was washed once with water and once with sodium carbonate solution. The aqueous 10 phases were individually extracted twice with ether. The organic phases were combined, dried over magnesium sulfate, filtered and the filtrate was evaporated completely. This gave 0.68 g of 4-(2,6-difluoro-4-propylphenyl)cyclohexanone.

e) 535 ml of diethylaminosulphur trifluoride (DAST) were added dropwise in 3 portions over 60 hours to a solution of 0.63 g of 4-(2,6-difluoro-4-propylphenyl)cyclohexanone in 15 ml of dimethoxyethane and 50 ml of trifluoromethanesulphonic acid. The reaction solution was subsequently partitioned between sodium carbonate solution and ether. The organic phase was washed twice with water and the aqueous phases were individually extracted twice with ether. The organic phases were combined, dried over magnesium sulfate, filtered and the filtrate was evaporated completely. The resulting crude product (0.8 g) was purified by chromatography and gave 0.36 g of 1-fluoro-4-(2,6-difluoro-4-propylphenyl)cyclohex-1-ene, m.p. (C/I) 62.5° C.

The following compounds can be prepared in an analogous manner:

1-fluoro-4-(2,6-difluoro-4-ethylphenyl)cyclohex-1 -ene;

1-fluoro-4-(2,6-difluoro-4-pentylphenyl)cyclohex-l-ene;

1-fluoro-4-[2,6-difluoro-4-(4-trans-propylcyclohexyl)phenyl]-cyclohex-1-ene;

1-fluoro-4- {2,6-difluoro-4-[2-(4-trans-propylcyclohexyl)ethyl]-phenyl } cyclohex-1 -ene;

1 -fluoro-4-[2,6-difluoro-4-(4-trans-butylcyclohexyl)phenyl]-cyclohex-1-ene, m.p. 75.5° C.;

1-fluoro-4-[trans-4-(2,6-difluoro-4-ethylphenyl)cyclohexyl]-cyclohex-1-ene;

1-fluoro-4-[trans-4-(2,6-difluoro-4-propylphenyl)cyclohexyl]-cyclohex-1-ene;

1-fluoro-4-[trans-4-(2,6-difluoro-4-pentylphenyl)cyclohexyl]-cyclohex-1-ene;

1-fluoro-4-{2-[trans-4-(2,6-difluoro-4-propylphenyl)cyclohexyl]ethyl}cyclohex- 1 -ene.

EXAMPLE 4 a) 2.01 g of 8-[trans-4-(2,6-difluoro-4-propylphenylethynyl)-cyclohexyl]-1,4-dioxa-spiro[4,5]decane are dissolved in 30 ml of ethyl acetate, treated with 0.2 g of 10% palladium on charcoal and hydrogenated at room temperature and under normal pressure until 0.01 mol of hydrogen has been taken up. Subsequently, the mixture is filtered over Celite and the clear solution is evaporated. This gives 8-{trans-4-[2-(2,6-difluoro-4-propylphenyl)-ethyl]cyclohexyl}-1,4-dioxa-spiro[4,5]decane.

b) 2 g of 8-{trans-4-[2-(2,6-difluoro-4-propylphenyl)ethyl]-cyclohexyl}-1,4-dioxa-spiro[4,5]decane from the previous step are taken up in 12 ml of 98% formic acid and 24 ml of toluene and stirred for 1 hour, thereafter the reaction solution is partitioned between water/ether. The organic phase is washed once with water and once with sodium carbonate solution. The aqueous phases are individually extracted twice with ether. The organic phases are combined, dried over magnesium sulfate, filtered and the filtrate is evaporated completely. This gives 4-{trans-4-[2-(2,6-difluoro-4-propylphenyl)ethyl]cyclohexyl}cyclohexanone.

c) 1.1 ml of diethylaminosulphur trifluoride (DAST) are added dropwise in 3 portions over 60 hours to a solution of 1.7 g of 4-{trans-4-[2-(2,6-difluoro-4-propylphenyl)ethyl]cyclohexyl}cyclohexanone in 30 ml of dimethoxyethane and 0.1 ml of trifluoromethanesulphonic acid. The reaction solution is subsequently partitioned between sodium carbonate solution/ether. The organic phase is washed twice with water and the aqueous phases are individually extracted twice with ether. The organic phases are combined, dried over magnesium sulfate, filtered and the filtrate is evaporated completely. The crude product obtained is chromatographed over silica gel and gives 1-fluoro-4-{trans-4-[2-(2,6-difluoro-4-propylphenyl)ethyl] cyclohexyl }cyclohex-1-ene.

In an analogous manner there can be prepared:

1-fluoro-4-{trans-4-[2-(2,6-difluoro-4-ethylphenyl)ethyl]cyclohexyl}cyclohex-1-ene;

1 -fluoro-4-{trans-4- [2-(2,6-difluoro-4-pentylphenyl)ethyl]cyclohexyl}cyclohex-1-ene;

1 -fluoro-4-{2-[2,6-difluoro-4-(trans-4-ethylcyclohexyl)phenyl]-ethyl}cyclohex-1-ene;

1-fluoro-4-{2-[2,6-difluoro-4-(trans-4-propylcyclohexyl)-phenyl]ethyl}cyclohex-1-ene;

1-fluoro-4-{2-[2,6-difluoro-4- (trans-4-pentylcyclohexyl)-phenyl]ethyl}cyclohex-1-ene.

EXAMPLE 5 a) A solution of 1.2 g of 1-fluoro-4-(trans-4-methoxycarbonylcyclohexyl)cyclohex-1-ene in 5 ml of dry tetrahydro-furan is added dropwise at 0° C. to a solution of 0.303 g of lithium aluminium hydride in 15 ml of dry tetrahydrofuran. Then, the mixture is stirred for one hour, 1 ml of ethyl acetate is added, the mixture is stirred for a further 30 minutes and subsequently acidified with 1N hydrochloric acid. Then, the mixture is diluted with 100 ml of water, extracted twice with methylene chloride and the combined organic phases are washed with sodium bicarbonate solution and with water. The organic phase is dried over magnesium sulfate, filtered, the filtrate is evaporated and the residue is chromatographed on silica gel. This gives 1-fluoro-4-(trans-4-hydroxymethylcyclohexyl)cyclohex-1-ene.

b) 2.11 g of bromotriphenylphosphonium bromide are added at room temperature to a solution of 0.95 g of 1-fluoro-4-(trans-4-hydroxymethylcyclohexyl)cyclohex-1-ene in 10 ml of aceto-nitrile and thereupon the mixture is stirred for 30 minutes. Then, the reaction mixture is evaporated completely, the residue is dissolved in a small amount of methylene chloride and this solution is diluted with a ten-fold amount of pentane. The resulting suspension is filtered over silica gel/Celite and the solution is evaporated completely. This gives 1-fluoro-4-(trans-4-bromomethyl-cyclohexyl)cyclohex-1-ene.

c) 1 g of finely ground potassium carbonate and a solution of 0.7 g of 2,6-difluoro-4-propylphenol in 5 ml of acetone are added to a solution of 1.1 g of 1-fluoro-4-(trans-4-bromo-methylcyclohexyl)-cyclohex-1-ene in 20 ml of acetone and the mixture is stirred at reflux temperature for 15 hours. Thereafter, the solvent is evaporated, the residue is partitioned between water and methylene chloride and the organic phase is dried over magnesium sulfate. Then, the solution is filtered, the filtrate is evaporated completely and the residue is chromatographed on silica gel. This gives 1-fluoro-4-[trans-4-(2,6-difluoro-4-propylphenoxymethyl)cyclohexyl]cyclohex-1-ene.

The following compounds can be prepared in an analogous manner:

1 -fluoro-4-[trans-4-(2,6-difluoro-4-ethylphenoxymethyl)cyclo-hexyl]cyclohex-1-ene;

1-fluoro-4-[trans-4-(2,6-difluoro-4-butylphenoxymethyl)cyclo-hexyl]cyclohex-1-ene;

1-fluoro-4-[trans-4-(2,6-difluoro-4-pentylphenoxymethyl)cyclo-hexyl]cyclohex-1-ene;

1-fluoro-4-[2,6-difluoro-4-(trans-4-propylcyclohexyl)phenoxy-methyl]cyclohex-1-ene;

1-fluoro-4-[2,6-difluoro-4-(trans-4-pentylcyclohexyl)phenoxy-methyl]cyclohex-1-ene;

1-fluoro-4-[2,6-difluoro-4-(trans-4-vinylcyclohexyl)phenoxy-methyl]cyclohex-1 -ene;

1-fluoro-4-[2,6-difluoro-4-(trans-4-(E)-propenylcyclohexyl)-phenoxymethyl]cyclohex-1-ene;

1-fluoro-4-{2,6-difluoro-4-[trans-4-(3-butenyl)cyclohexyl]-phenoxymethyl}cyclohex-1-ene.

EXAMPLE 6

Binary mixtures (BM) with 4-(trans-4-pentylcyclohexyl)-benzonitrile were prepared in order to investigate the properties of the compounds of formula I in mixtures. The threshold potential and the response times were measured at 22° C. in a TN cell (low bias tilt) having a plate separation of 8 mm; the 2.5-fold value of the threshold potential ($V_{10}$) was chosen as the operating voltage. The corresponding data for 4-(trans-4-pentyl-cyclohexyl)benzonitrile are: cl.p. (N-I) =54.6° C., $V_{10}$=1.62 V, $t_{on}$=22ms, $t_{off}$=42 ms, $\Delta n$=0.120.

BM-1

90 wt. % of 4-(trans-4-pentyl-cyclohexyl)benzonitrile 10 wt. % of 1-fluoro-4-[trans-4-(2,6-difluoro-4-propyl-phenylethynyl)cyclohexyl]cyclohex-1-ene c.l.p. (N/I): 55.0° C., $V_{10}$=1.53 V, $t_{on}$=29 ms, $t_{off}$=46 ms, $\Delta n$=0.123

BM-2

80 wt. % of 4-(trans-4-pentyl-cyclohexyl)benzonitrile 20 wt. % of 1-fluoro-4-[trans-4-(2,6-difluoro-4-propyl-phenylethynyl)cyclohexyl]cyclohex-1-ene c.l.p. (N/I): 56.1° C., $V_{10}$=1.47 V, $t_{on}$=33 ms, $t_{off}$=52 ms, $\Delta n$=0.121

BM-3

90 wt. % of 4-(trans-4-pentyl-cyclohexyl)benzonitrile 10 wt. % of trans-4-(1-fluorocyclohex-1-en-4-yl)cylohexanoyl 2,6-difluoro-4-propylphenolate cl.p. (N/I): 54.1° C., $V_{10}$=1.46 V, $t_{on}$=36 ms, $t_{off}$=48 ms, $\Delta n$=0.116

BM-4

80 wt. % of 4-(trans-4-pentyl-cyclohexyl)benzonitrile 20 wt. % of trans-4-(1-fluorocyclohex-1-en-4-yl)cylohexanoyl 2,6-difluoro-4-propylphenolate cl.p. (N/I): 55.7° C., $V_{10}$=1.38 V, $t_{on}$=43 ms, $t_{off}$=59 ms, $\Delta n$=0.111

BM-5

90 wt. % of 4-(trans-4-pentyl-cyclohexyl)benzonitrile 10 wt. % of 1-fluoro-4-[2,6-difluoro-4-(4-trans-butyl-cyclohexyl)phenyl]cyclohex-1-ene cl.p. (n/i): 47.9° C., $V_{10}$=1.45 V, $t_{on}$=31 ms, $t_{off}$=51 ms, $\Delta n$=0.114

BM-6

80 wt. % of 4-(trans-4-pentyl-cyclohexyl)benzonitrile 20 wt. % of 1-fluoro-4-[2,6-difluoro-4-(4-trans-butyl-cyclohexyl)phenyl]cyclohex-1-ene cl.p. (N/I): 40.9° C., $V_{10}$=1.29 V, $t_{on}$=42 ms, $t_{off}$=69 ms, $\Delta n$=0.103

We claim:

1. A compound of the formula

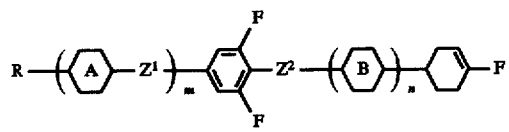

I wherein

R is $C_1$–$C_7$ alkyl or $C_2$–$C_{12}$ alkenyl;

rings A and B each independently are 1,4-phenylene, trans-1,4-cyclohexylene or trans-1,3-dioxane-2,5-diyl;

$Z^1$ is a single bond or —$CH_2CH_2$—; and $Z^2$ is a single bond, —$CH_2CH_2$—, —$OCH2$—, —C≡C—, —COO— or —OOC—; and m, n are 0 or 1, with the proviso that m+n≦1.

2. A compound according to claim 1 of the formula

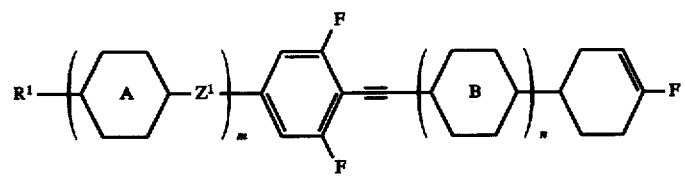

I-A

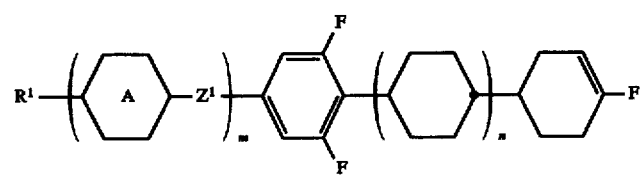

I-B

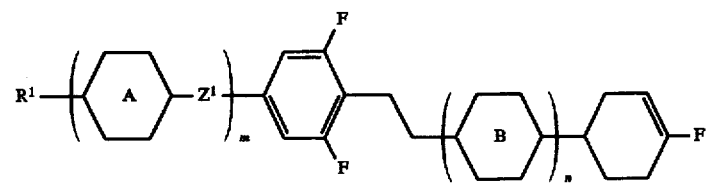

I-C

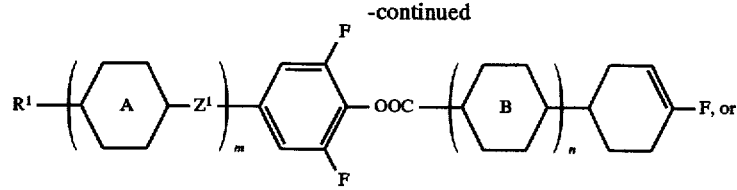
I-D

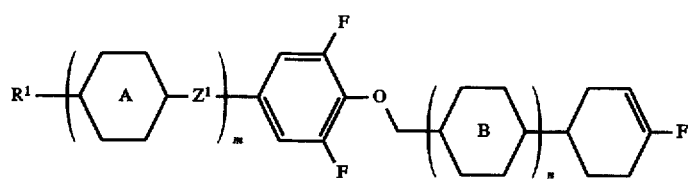
I-E wherein R¹ is $C_1$–$C_7$, alkyl, $C_4$–$C_7$ 3E-alkenyl or on a saturated ring also vinyl or $C_2$–$C_7$ 1E-alkenyl.

3. A compound according to claim 2 of the formula

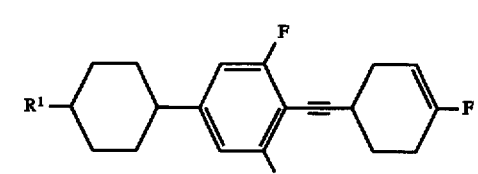
I-A1

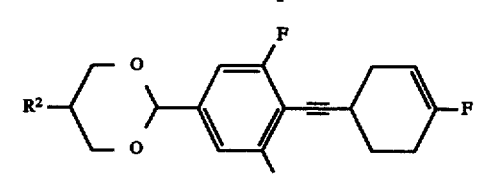
I-A2

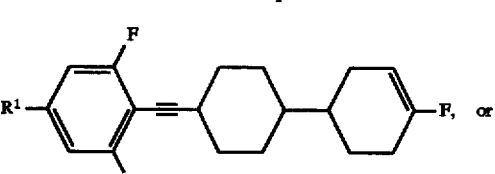
I-A3

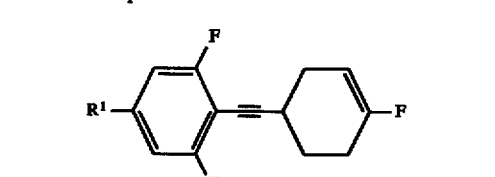
I-A4 wherein R¹ is $C_1$–$C_7$ alkyl, $C_4$–$C_7$ 3E-alkenyl or on a saturated ring also vinyl or $C_2$–$C_7$ 1E-alkenyl.

4. A compound according to claim 2 of the formula

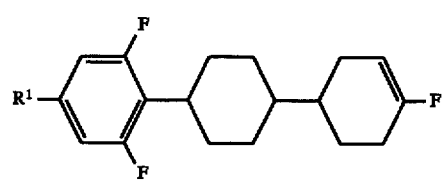
I-B1

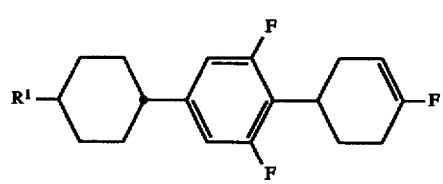
I-B2

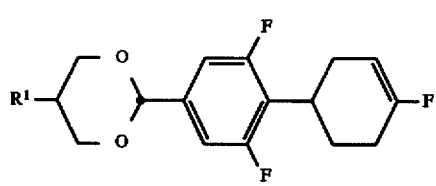
I-B3

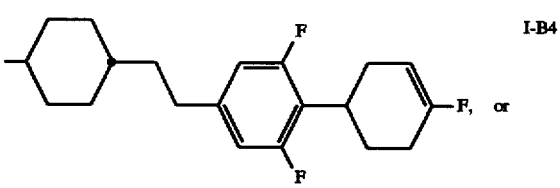
I-B4

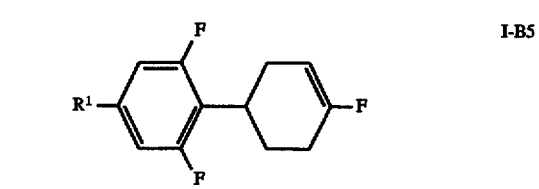
I-B5 wherein R¹ is $C_1$–$C_7$ alkyl, $C_4$–$C_7$ 3E-alkenyl or on a saturated ring also vinyl or $C_2$–$C_7$ 1E-alkenyl.

5. A compound according to claim 2 of the formula

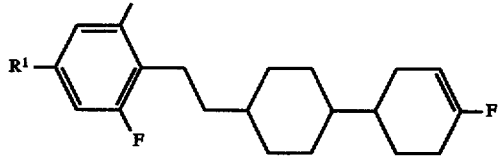
I-C1

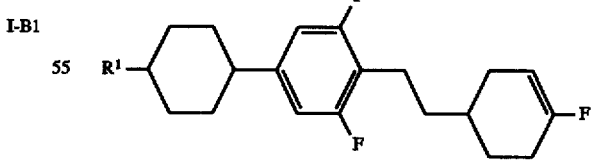
I-C2

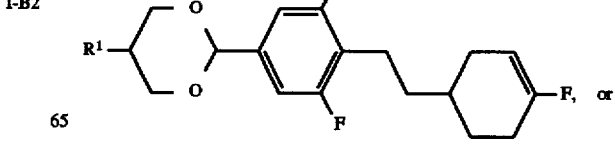
I-C3

I-C4

[structure: R¹–(2,6-difluorophenyl)–CH₂CH₂–cyclohexenyl–F]

wherein R¹ is C₁–C₇ alkyl, C₄–C₇ 3E-alkenyl or on a saturated ring also vinyl or C₂–C₇ 1E-alkenyl.

6. A compound according to claim 2 of the formula

I-D1

[structure: R¹–(2,6-difluorophenyl)–OOC–cyclohexyl–cyclohexenyl–F], or

I-D2

[structure: R¹–cyclohexyl–(2,6-difluorophenyl)–OOC–cyclohexenyl–F]

wherein R¹ is C₁–C₇ alkyl, C₄–C₇ 3E-alkenyl or on a saturated ring also vinyl or C₂–C₇ 1E-alkenyl.

7. A compound according to claim 2 of the formula

I-E1

[structure: R¹–(2,6-difluorophenyl)–O–CH₂–cyclohexyl–cyclohexenyl–F], or

I-E2

[structure: R¹–cyclohexyl–(2,6-difluorophenyl)–O–CH₂–cyclohexenyl–F]

wherein R¹ is C₁–C₇ alkyl, C₄–C₇ 3E-alkenyl or on a saturated ring also vinyl or C₂–C₇ 1E-alkenyl.

8. A compound according to claim 1, wherein R¹ is ethyl, propyl, butyl, pentyl, 3-butenyl or 3E-pentenyl and on trans-1,4-cyclohexylene or trans-1,3-dioxane-2,5-diyl also vinyl, 1E-propenyl, 1E-butenyl or 1E-pentenyl.

9. The compound according to claim 3, 1-fluoro-4-[trans-4-(2,6-difluoro-4-propylphenylethynyl)cyclohexyl]cyclohex-1-ene.

10. The compound according to claim 4, 1-fluoro-4-(2,6-difluoro-4-propylphenyl)cyclohex-1-ene.

11. The compound according to claim 6, trans-4-(1-fluorocyclohex-1-en-4-yl)cyclohexanoyl 2,6-difluoro-4-propylphenolate.

12. A compound according to claim 1, wherein R is propyl, m is 0, n is 1 and ring B is trans-1,4-cyclohexylene.

13. A liquid crystalline mixture having at least 2 components, wherein at least one component is a compound of the

I

[structure: R–(A)–Z¹–ₘ–(2,6-difluorophenyl)–Z²–(B)–ₙ–F]

wherein

R is C₁–C₇ alkyl or C₂–C₁₂ alkenyl;

rings A and B each independently are 1,4-phenylene, trans-1,4-cyclohexylene or trans-1,3-dioxane-2,5-diyl;

Z¹ is a single bond or —CH₂CH₂—; and

Z² is a single bond, —CH₂CH₂—, —OCH₂—, —C≡C—, —COO— or —OOC—; and m, n are 0 or 1, with the proviso that m+n≦1.

14. A liquid crystalline mixture according to claim 13, wherein the content of compounds of formula I is 1–70 wt. %.

15. A liquid crystalline mixture according to claim 14, wherein the content of compounds of formula I is 5–20 wt. %.

16. A liquid crystalline mixture according to claim 13, wherein the at least one component is a compound of formula I wherein R is propyl, m is 0, n is 1, and ring B is trans-1,4-cyclohexylene.

* * * * *